United States Patent
Nishi et al.

(10) Patent No.: US 12,376,746 B2
(45) Date of Patent: Aug. 5, 2025

(54) OPHTHALMIC DEVICE AND TOMOGRAPHIC IMAGE GENERATION DEVICE

(71) Applicants: NIKON CORPORATION, Tokyo (JP); OPTOS PLC, Dunfermline Fife (GB)

(72) Inventors: Yasufumi Nishi, Edinburgh (GB); Alistair Gorman, Dunfermline (GB)

(73) Assignees: NIKON CORPORATION, Tokyo (JP); OPTOS PLC, Dunfermline Fife (GB)

( * ) Notice: Subject to any disclaimer, the term of this patent is extended or adjusted under 35 U.S.C. 154(b) by 566 days.

(21) Appl. No.: 17/537,300

(22) Filed: Nov. 29, 2021

(65) Prior Publication Data
US 2022/0079434 A1    Mar. 17, 2022

Related U.S. Application Data

(63) Continuation of application No. PCT/JP2020/020945, filed on May 27, 2020.

(30) Foreign Application Priority Data

May 31, 2019    (JP) .................. 2019-102476

(51) Int. Cl.
*A61B 3/12* (2006.01)
*A61B 3/10* (2006.01)

(52) U.S. Cl.
CPC ............ *A61B 3/1225* (2013.01); *A61B 3/102* (2013.01)

(58) Field of Classification Search
CPC ..... A61B 3/1225; A61B 3/102; A61B 3/1025; A61B 3/0008; A61B 3/0016; A61B 3/12; A61B 3/14

(Continued)

(56) References Cited

U.S. PATENT DOCUMENTS

2008/0106696 A1    5/2008  Buckland et al.
2015/0085358 A1*   3/2015  Merz ............. A61B 3/12
                                               359/381

(Continued)

FOREIGN PATENT DOCUMENTS

CN    102657514 A    9/2012
EP    2 926 722 A1   10/2015

(Continued)

OTHER PUBLICATIONS

Li et al. (CN 102657514) Portable Retinal Imaging Instrument (Year: 2014).*

(Continued)

*Primary Examiner* — Wyatt A Stoffa
*Assistant Examiner* — Rahman Abdur
(74) *Attorney, Agent, or Firm* — Foley & Lardner LLP

(57) ABSTRACT

An ophthalmic device includes a scanning member, an objective lens, and an optical element. The objective lens includes a first lens group and a second lens group in order from the scanning member side. The optical element is capable of being inserted into and removed from an optical path between the second lens group of the objective lens and the scanning member. In a case in which the optical element is not inserted into the optical path, the objective lens configures a first observation optical system. In a case in which the optical element has been inserted into the optical path, the objective lens and the optical element configure a second observation optical system.

6 Claims, 10 Drawing Sheets

(58) Field of Classification Search
USPC .......................................................... 351/206
See application file for complete search history.

(56) References Cited

U.S. PATENT DOCUMENTS

2015/0313467 A1* 11/2015 Sakai ..................... A61B 3/152
                                                          351/208
2016/0317028 A1    11/2016 Murata et al.

FOREIGN PATENT DOCUMENTS

| JP | 2016-028682 A | 3/2016 |
| JP | 2016-032578 A | 3/2016 |
| JP | 2017-200613 A | 11/2017 |
| JP | 2018-196823 A | 12/2018 |
| JP | 2019-080867 A | 5/2019 |

OTHER PUBLICATIONS

JP Office Action on JP Appl. Ser. No. 2021-571487 dated Oct. 4, 2022 (6 pages).
Office Action issued in corresponding Japanese Patent Application No. 2021-571487 dated Jun. 13, 2023 (5 pages).
CN Office Action issued in corresponding CN Application No. 202080040056.3 Dated Jan. 26, 2025 (21 pages).
Office Action issued in corresponding Australian Application No. 2023278112 dated Jan. 10, 2025 (3 pages).

* cited by examiner

FIG.5
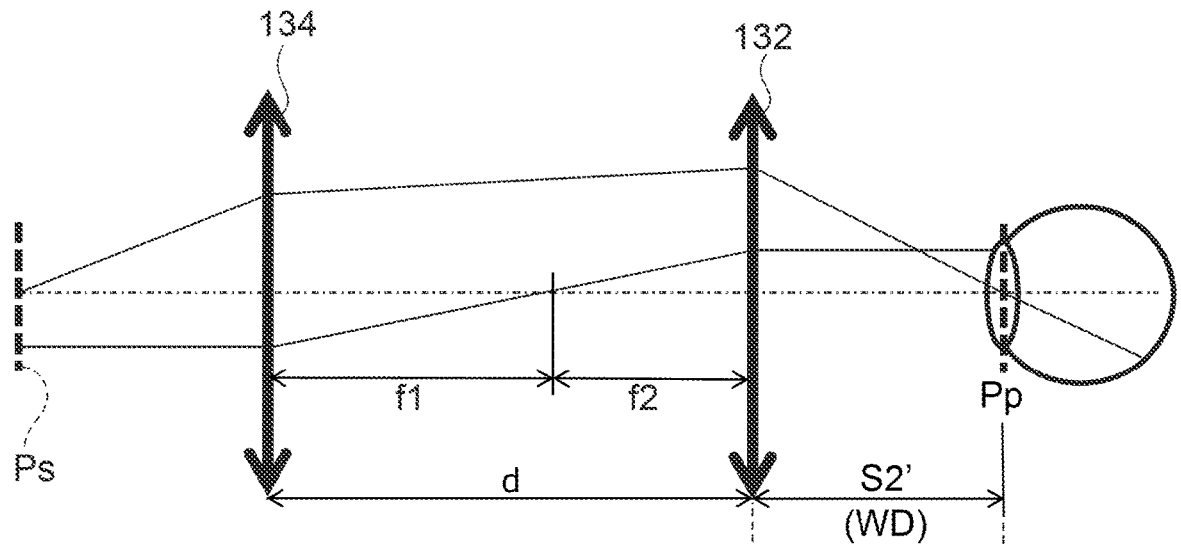
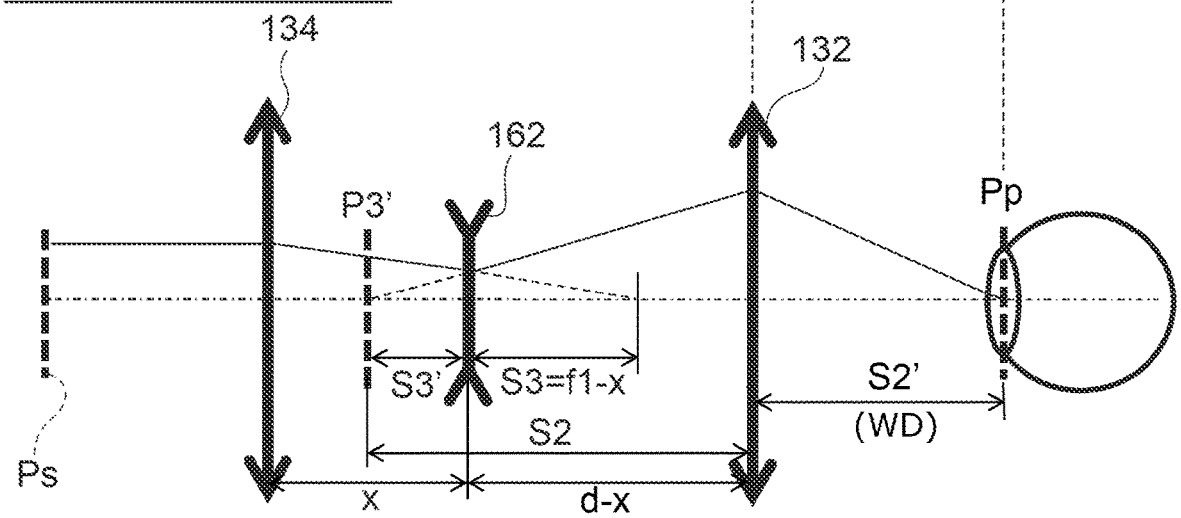

FIG.10
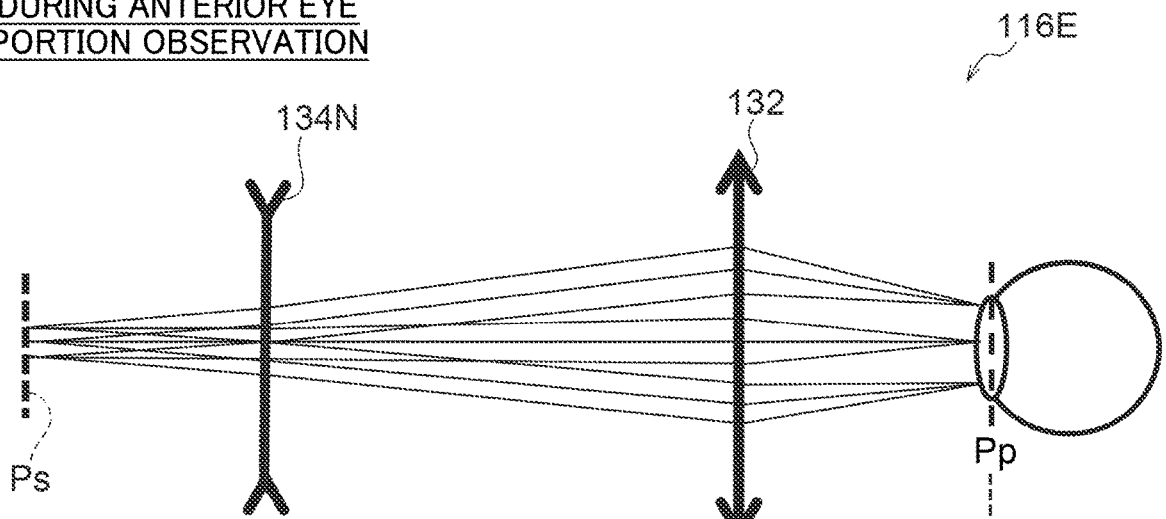
DURING ANTERIOR EYE PORTION OBSERVATION
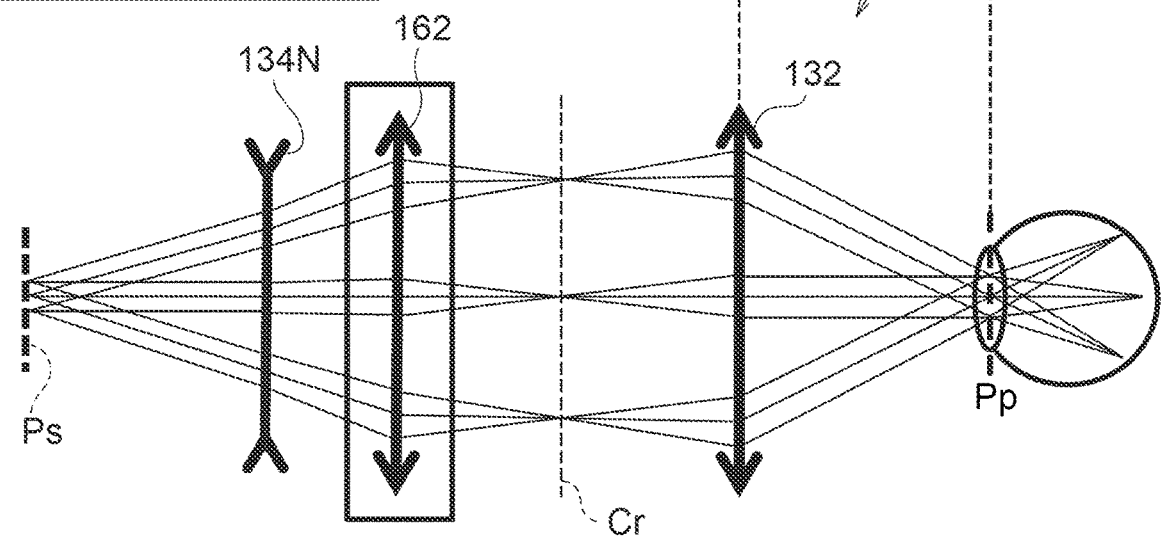
DURING POSTERIOR EYE PORTION OBSERVATION

US 12,376,746 B2

OPHTHALMIC DEVICE AND TOMOGRAPHIC IMAGE GENERATION DEVICE

CROSS-REFERENCE TO RELATED APPLICATIONS

This application is a continuation application of International Application No. PCT/JP2020/020945, filed May 27, 2020, the disclosure of which is incorporated herein by reference in its entirety. Further, this application claims priority from Japanese Patent Application No. 2019-102476, filed May 31, 2019, the disclosure of which is incorporated herein by reference in its entirety.

TECHNICAL FIELD

The present invention relates to an ophthalmic device and a tomographic image generation device.

BACKGROUND ART

In a known configuration of an optical coherence tomography device for acquiring a tomographic image of a posterior eye portion such as an ocular fundus of an examined eye, a lens attachment is disposed between an objective lens and the examined eye, and a tomographic image of an anterior eye portion such as the cornea or the like is acquired (United States Patent Application Laid-Open No. 2008/0106696). By employing a lens attachment in such an optical coherence tomography device, tomographic images can be acquired for both a posterior eye portion and an anterior eye portion of an examined eye using a single device.

In the conventional optical coherence tomography device mentioned above, the lens attachment is disposed between the examined eye and the objective lens, and so alignment between a subject of examination and the imaging device needs to be re-adjusted every time a switch is made from posterior eye portion observation to anterior eye portion observation.

SUMMARY OF INVENTION

An ophthalmic device of a first aspect of the technology disclosed herein comprises a scanning member for scanning light that has been emitted from a light source; an objective lens comprising a first lens group and a second lens group in order from the scanning member side, the second lens group being a lens group having a positive power; and an optical element that is capable of being inserted into and removed from an optical path between the second lens group of the objective lens and the scanning member, wherein: in a case in which the optical element is not inserted into the optical path, the objective lens configures a first observation optical system, and light that is scanned by the scanning member is focused in a first region of an examined eye, and in a case in which the optical element has been inserted into the optical path, the objective lens and the optical element configure a second observation optical system, and light that is scanned by the scanning member is focused in a second region that is different from the first region of the examined eye.

An optical tomographic image generation device of a second aspect of the technology disclosed herein, comprises a light source that generates light for optical coherence tomography (OCT); a dividing section that divides light from the light source into measurement light and reference light; a scanning member for scanning the measurement light; an objective lens comprising a first lens group and a second lens group in order from a scanning member side, the second lens group being a lens group having a positive power; an optical element that is capable of being inserted into and removed from an optical path between the second lens group of the objective lens and the scanning member; an interference light detector that detects interference light obtained by synthesis of return light from an examined eye and the reference light; and an image generation section that generates a tomographic image of the examined eye based on the interference light detected by the detector, wherein: in a case in which the optical element is not inserted into the optical path, the objective lens configures a first observation optical system, and light that is scanned by the scanning member is focused in a first region of the examined eye, and in a case in which the optical element has been inserted into the optical path, the objective lens and the optical element configure a second observation optical system, and light that is scanned by the scanning member is focused in a second region of the examined eye.

BRIEF DESCRIPTION OF DRAWINGS

FIG. 5 are optical configuration diagrams using a thin system to illustrate a basic configuration of an image capture optical system of the first exemplary embodiment, and illustrate a configuration diagram for a case in which a negative lens is not inserted on the optical path between two positive power lens groups (top), and a configuration diagram for a case in which a negative lens is inserted thereon (bottom).

FIG. 10 are optical configuration diagrams using a thin system to illustrate a basic configuration of an image capture optical system of a third exemplary embodiment, and illustrate an optical configuration diagram using a thin system to illustrate a state in which anterior eye portion observation is possible using a negative first lens group and a positive second lens group (top diagram) and an optical configuration diagram using a thin system to illustrate a state in which posterior eye portion observation is possible with a switching lens that is a lens having a positive power inserted on the optical path between the negative first lens group and the positive second lens group (bottom diagram).

DESCRIPTION OF EMBODIMENTS

Detailed description follows regarding exemplary embodiments of the present invention, with reference to the drawings.

First Exemplary Embodiment

Figure 1:
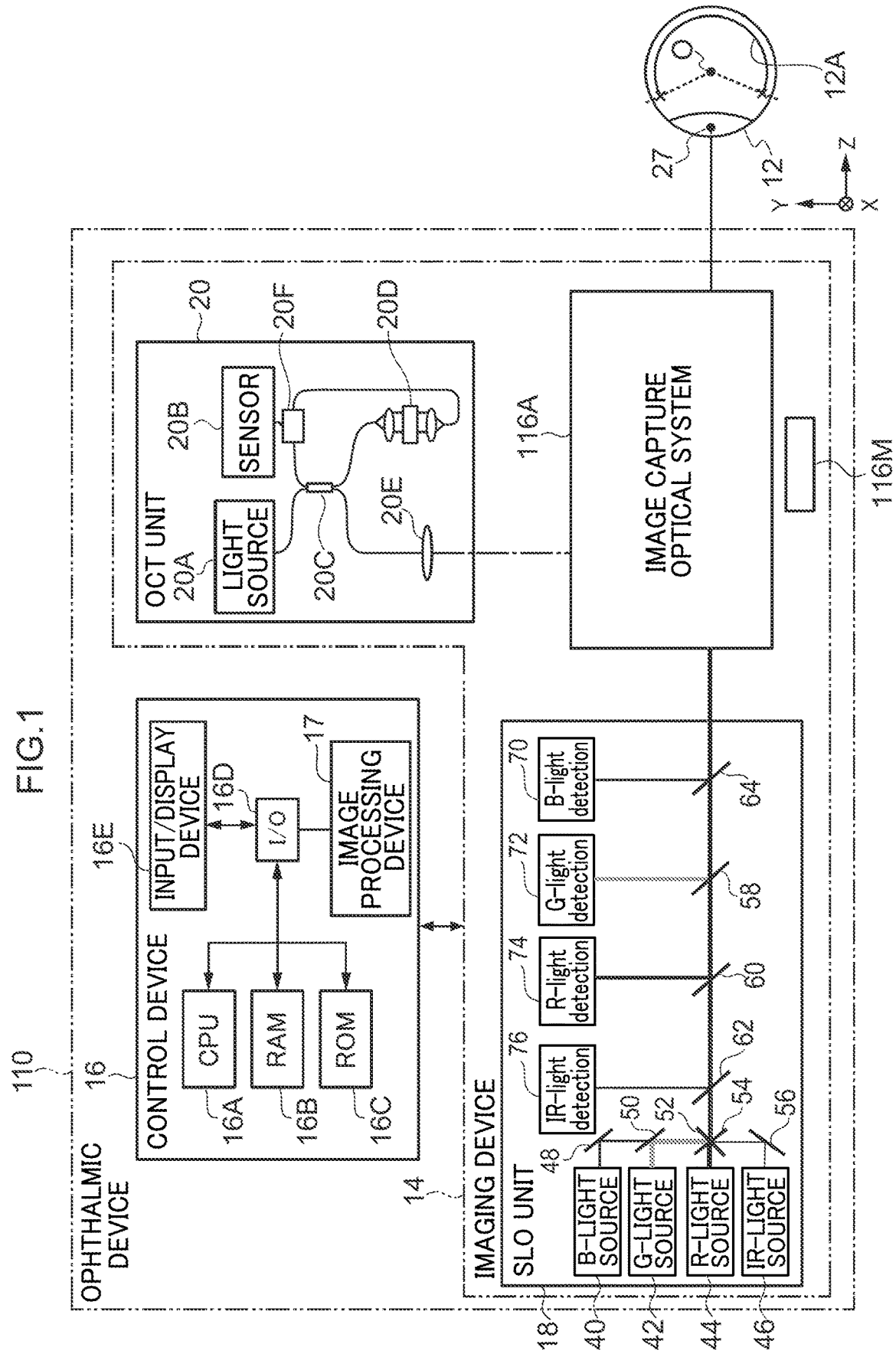
FIG. 1 is a schematic configuration diagram of an ophthalmic device of a first exemplary embodiment.

Description follows regarding an ophthalmic device 110 according to a first exemplary embodiment of the present invention, with reference to the drawings. FIG. 1 illustrates a schematic configuration of the ophthalmic device 110.

For ease of explanation, scanning laser ophthalmoscope is referred to as SLO and optical coherence tomography is referred to as OCT.

In cases in which the ophthalmic device 110 is installed on a horizontal plane with a horizontal direction taken as an X direction, a direction perpendicular to the horizontal plane is denoted as being a Y direction, and an optical axis direction of an image capture optical system 116A is denoted as being a Z direction. The device is disposed with respect to an examined eye such that the center of the pupil of the examined eye is positioned on the optical axis in the Z direction. The X direction, the Y direction, and the Z direction are thus mutually perpendicular directions.

The ophthalmic device 110 includes an imaging device 14 and a control device 16. The imaging device 14 is provided with an SLO unit 18 for acquiring an image of an ocular fundus 12A of an examined eye 12, and with an OCT unit 20 for acquiring a tomographic image of the examined eye 12. Ocular fundus images generated based on SLO data acquired by the SLO unit 18 are referred to hereafter as SLO images. Moreover, tomographic images generated based on OCT data acquired by the OCT unit 20 are referred to hereafter as OCT images. Note that the SLO images are also sometimes referred to as two-dimensional ocular fundus images. Moreover, the OCT images are also sometimes referred to as ocular fundus tomographic images or anterior eye portion tomographic images, depending on the imaging site on the examined eye 12.

The ophthalmic device 110 is an example of an "optical tomographic image generation device" of the technology disclosed herein.

The control device 16 includes a computer provided with a Central Processing Unit (CPU) 16A, Random Access Memory (RAM) 16B, Read-Only Memory (ROM) 16C, and an input/output (I/O) port 16D.

The control device 16 is provided with an input/display device 16E coupled to the CPU 16A through the I/O port 16D. The input/display device 16E includes a graphical user interface to display images of the examined eye 12 and to receive various instructions from a user. The input/display device 16E may employ a touch panel display.

The control device 16 is provided with an image processing device 17 coupled to the I/O port 16D. The image processing device 17 generates images of the examined eye 12 based on data acquired by the imaging device 14.

The image processing device 17 is an example of a "generation section" of technology disclosed herein.

Although the control device 16 of the ophthalmic device 110 is provided with the input/display device 16E as illustrated in FIG. 1 and described above, the technology disclosed herein is not limited thereto. For example, a configuration may ad opted in which the control device 16 of the ophthalmic device 110 is not provided with the input/display device 16E, and instead a separate input/display device that is physically independent of the ophthalmic device 110 is provided. In such cases, the display device is provided with an image processing processor unit that operates under the control of the CPU 16A in the control device 16. Such an image processing processor unit may display SLO images and the like based on an image signal output as an instruction by the CPU 16A.

The imaging device 14 operates under the control of the control device 16. The imaging device 14 includes the SLO unit 18, an image capture optical system 116A, and the OCT unit 20. The image capture optical system 116A is moved in the X, Y, Z directions by an image capture optical system drive section 116M under control by the CPU 16A. Alignment (positional alignment) between the imaging device 14 and the examined eye 12 may be performed, for example, not only by moving the imaging device 14 alone, but also by moving the entire ophthalmic device 110 in the X, Y, Z directions.

An SLO system is implemented by the control device 16, the SLO unit 18, a nd the image capture optical system 116A illustrated in FIG. 1.

The SLO unit 18 include plural light sources. For example, as illustrated in FIG. 1, the SLO unit 18 include a B-light (blue light) source 40, a G-light (green light) source 42, an R-light (red light) source 44, an IR-light (infrared light (for example near infrared light)) source 46. Light emitted from each of the light sources 40, 42, 44, 46 is directed onto a single optical path by respective optical members 48, 50, 52, 54, 56. The optical members 48, 56 are configured by mirrors, and the optical members 50, 52, 54 are configured by beam splitters. B-light is guided through the optical members 48, 50, 54 and onto the optical path of the image capture optical system 116A. G-light is guided through the optical members 50, 54 and onto the optical path of the image capture optical system 116A. R-light is guided through the optical members 52, 54 and onto the optical path of the image capture optical system 116A. IR-light is guided through the optical members 56, 52 and onto the optical path of the image capture optical system 116A. Note that LED light sources and laser light sources may be employed as the light sources 40, 42, 44, 46. Note that the following description is of an example in which laser light sources are employed therefor. Total reflection mirrors may be employed as the optical members 48, 56. Moreover, dichroic mirrors, half-mirrors, or the like may be employed as the optical members 50, 52, 54.

The light sources 40, 42, 44, 46 are examples of "laser light sources" of technology disclosed herein.

The SLO unit 18 is configured so as to be capable of switching between various light emission modes such as a light emission mode in which G-light, R-light, B-light, and IR-light are separately emitted, a light emission mode in which all of these lights are emitted at the same time or a number of these lights are emitted at the same time, and the like. Although the example illustrated in FIG. 1 includes four light sources, i.e. the B-light (blue light) light source 40, the G-light light source 42, the R-light light source 44, and the IR-light light source 46, the technology disclosed herein is not limited thereto. For example, the SLO unit 18 may further include a white-light light source. In such cases a light emission mode in which white light is emitted alone, or the like, may also be set in addition to the various light emission modes listed above.

Laser light introduced into the image capture optical system 116A from the SLO unit 18 is scanned in the X direction and the Y direction by scanning sections (120, 142), described later. The scanned light passes through the pupil 27 and is irradiated onto a posterior eye portion (for example, an ocular fundus 12A) of the examined eye 12. Reflected light that has been reflected by the ocular fundus 12A is introduced into the SLO unit 18 through the image capture optical system 116A.

The scanning sections (120, 142) are examples of "scanning members" of technology disclosed herein.

The reflected light that has been reflected at the ocular fundus 12A is detected by light detection elements 70, 72, 74, 76 provided in the SLO unit 18. In the present exemplary embodiment the SLO unit 18 includes the B-light detection element 70, the G-light detection element 72, the R-light detection element 74, and the IR-light detection element 76 corresponding to the plural light sources, namely, the B-light source 40, the G-light source 42, the R-light source 44, and the IR-light source 46. The B-light detection element 70 detects B-light reflected at the beam splitter 64. The G-light detection element 72 detects G-light that has passed through the beam splitter 64 and been reflected at the beam splitter 58. The R-light detection element 74 detects R-light that has passed through the beam splitters 64, 58 and been reflected at the beam splitter 60. The IR-light detection element 76 detects IR-light that has passed through the beam splitters 64, 58, 60 and been reflected at the beam splitter 62. Avalanche photodiodes (APD) may, for example, be employed as the light detection elements 70, 72, 74, 76.

The light detection elements 70, 72, 74, 76 are examples of "laser light detectors" of the technology disclosed herein.

Under control of the CPU 16A, the image processing device 17 generates SLO images corresponding to each color using signals respectively detected by the B-light detection element 70, the G-light detection element 72, the R-light detection element 74, and the IR-light detection element 76. The SLO images corresponding to each color include a B-SLO image generated using a signal detected by the B-light detection element 70, a G-SLO image generated using a signal detected by the G-light detection element 72, an R-SLO image generated using a signal detected by the R-light detection element 74, and an IR-SLO image generated using a signal detected by the IR-light detection element 76. Moreover, when in a light emission mode in which the B-light source 40, the G-light source 42, and the R-light source 44 emit light at the same time, an RGB-SLO image may be synthesized from the R-SLO image, the G-SLO image, and the B-SLO image generated using the respective signals detected by the R-light detection element 74, the G-light detection element 72, and the B-light detection element 70. Moreover, when in a light emission mode in which the G-light source 42 and the R-light source 44 emit light at the same time, an RG-SLO image may be synthesized from the R-SLO image and the G-SLO image generated using the respective signals detected by the R-light detection element 74 and the G-light detection element 72. Although in the first exemplary embodiment an R G-SLO image is employed as the SLO image, there is no limitation thereto, and another SLO image may be employed.

Dichroic mirrors, half-mirrors, or the like may be employed as the beam splitters 58, 60, 62, 64.

An OCT system is a three-dimensional image acquisition device realized by the control device 16, the OCT unit 20, and the image capture optical system 116A illustrated in FIG. 1. The OCT unit 20 includes a light source 20A, a sensor (detection element) 20B, a first optical coupler 20C, a reference light optical system 20D, a collimator lens 20E, and a second optical coupler 20F.

The first optical coupler 20C is an example of a "dividing section" of technology disclosed herein. The sensor (detection element) 20B is an example of an "interference light detector" of technology disclosed herein.

The light source 20A generates light for optical coherence tomography. A super luminescent diode (SLD) or the like may, for example, be employed as the light source 20A. The light source 20A emits light of low coherence from a broad band light source having wide spectral width. The light emitted from the light source 20A is divided at the first optical coupler 20C. After one division of the divided light has been made into parallel light by the collimator lens 20E, to serve as measurement light, the parallel light is introduced into the image capture optical system 116A. The measurement light is scanned in the X direction and the Y direction by scanning sections (148, 142), described later. The scanned light is irradiated onto the posterior eye portion through the anterior eye portion of the examined eye and the pupil 27. Measurement light that has been reflected at the anterior eye portion or the posterior eye portion passes through the image capture optical system 116A and is introduced into the OCT unit 20. The measurement light then passes through the collimator lens 20E and the first optical coupler 20C before being incident to the second optical coupler 20F. Note that although in the present exemplary embodiment an example is given of SD-OCT employing an SLD as the light source 20A, technology disclosed herein is not limited thereto, and SS-OCT employing a wavelength swept light source instead of the SLD may be adopted.

The other division of the light emitted from the light source 20A and divided by the first optical coupler 20C is introduced as reference light into the reference light optical system 20D, and is made incident to the second optical coupler 20F through the reference light optical system 20D.

The measurement light (return light) reflected and scattered by the examined eye 12 is combined with the reference light by the second optical coupler 20F to generate interference light. The interference light is detected by the sensor 20B. The image processing device 17 generates a tomographic image of the examined eye 12 based on a detection signal (OCT data) from the sensor 20B.

In the first exemplary embodiment the OCT system generates a tomographic image of an anterior eye portion or a posterior eye portion of the examined eye 12.

The anterior eye portion of the examined eye 12 is a section serving as an anterior eye segment including, for example, the cornea, the iris, the angle, the lens, the ciliary body, and a portion of the vitreous body. The posterior eye portion of the examined eye 12 is a section serving as a posterior eye segment including, for example, the remaining portion of the vitreous body, the retina, the choroid, and the sclera. Note that the anterior eye portion of the vitreous body is a section in the vitreous body at the cornea side of a boundary of an X-Y plane passing through a nearest point of the lens to the eyeball center, and the posterior eye portion of the vitreous body is a section in the vitreous body that is not the vitreous body of the anterior eye portion.

The OCT system generates, for example, a tomographic image of the cornea when the anterior eye portion of the examined eye 12 is the imaging target site. Moreover, the OCT system generates, for example, a tomographic image of the retina when the posterior eye portion of the examined eye 12 is the imaging target site.

The posterior eye portion and the anterior eye portion are respective examples of a "first region" and a "second region" of the technology disclosed herein.

Figure 2:
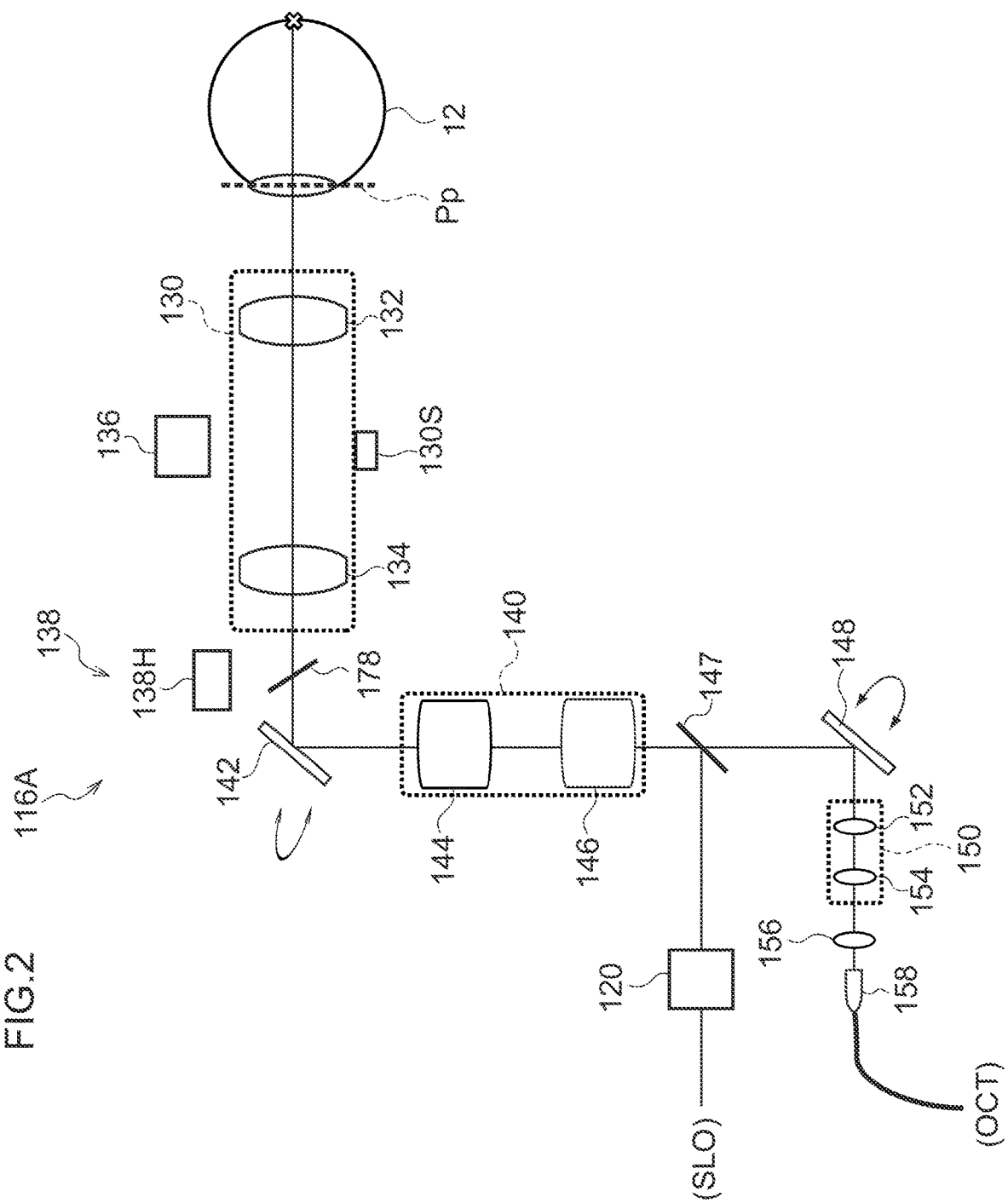
FIG. 2 is a schematic configuration diagram of an image capture optical system of the first exemplary embodiment.

FIG. 2 illustrates a schematic configuration diagram of the image capture optical system 116A. The image capture optical system 116A includes an objective lens 130, a beam splitter 178, a horizontal scanning section 142, a relay lens device 140, a beam splitter 147, vertical scanning sections 120, 148, a focus adjustment device 150, and a collimator lens 156, disposed in order from the examined eye 12 side.

Dichroic mirrors, half-mirrors, or the like may, for example, be employed as the beam splitters 178, 147.

The horizontal scanning section 142 is an optical scanner for horizontal-direction scanning of SLO scanning laser light or of OCT measurement light introduced through the relay lens device 140. In the present exemplary embodiment the horizontal scanning section 142 employed is common to both an SLO optical system and an OCT optical system, however, there is no limitation thereto. A horizontal scanning section may be respectively provided in each of the SLO optical system and the OCT optical system.

The collimator lens 156 takes light that was emitted from the OCT unit 20, propagated through a fiber and emitted from the fiber end 158 as the measurement light, and makes this parallel light.

The focus adjustment device 150 includes plural lenses 152, 154. The focus position of the measurement light in the examined eye 12 is adjusted by appropriately moving the plural lenses 152, 154 respectively along the optical axis direction ac cording to the imaging site in the examined eye 12. Note that although not illustrated in the drawings, in cases in which a focus detection device is provided, the lenses 152, 154 may be driven by a focus adjustment device according to a state of focus detection, so as to implement an autofocus device that performs focusing automatic ally.

The vertical scanning section 148 is an optical scanner for vertical-direction scanning the measurement light introduced through the focus adjustment device 150.

The vertical scanning section 120 is an optical scanner for vertical-direction scanning the laser light introduced from the SLO unit 18.

The relay lens device 140 includes the plural positive power lenses 144, 146. The relay lens device 140 is configured by the plural lenses 144, 146 such that positions of the vertical scanning sections 148, 120 are conjugate to a position of the horizontal scanning section 142. More specifically, the relay lens device 140 is configured such that positions of the center of the scanning angles of both scanning sections are conjugate to each other.

The beam splitter 147 is disposed between the relay lens device 140 and the vertical scanning section 148. The beam splitter 147 is an optical member that combines the SLO optical system and the OCT optical system. The beam splitter 147 reflects the SLO light emitted from the SLO unit 18 toward the relay lens device 140, and transmits the measurement light emitted from the OCT unit 20 toward the relay lens device 140. The measurement light emitted from the OCT unit 20 is two-dimensionally scanned by the vertical scanning section 148 and the horizontal scanning section 142. The light emitted from the SLO unit 18 is two-dimensionally scanned by the vertical scanning section 120 configuring the SLO optical system and the horizontal scanning section 142. The two-dimensionally scanned OCT measurement light and the two-dimensionally scanned SLO laser light are respectively introduced in to the examined eye 12 through the objective lens 130 configuring a common optical system. The SLO laser light reflected at the examined eye 12 is introduced into the SLO unit 18 via the objective lens 130, the horizontal scanning section 142, the relay lens device 140, the beam splitter 147, and the vertical scanning section 120. The OCT measurement light that has passed through the examined eye 12 is introduced into the OCT unit 20 via the objective lens 130, the horizontal scanning section 142, the relay lens device 140, the beam splitter 147, the vertical scanning section 148, the focus adjustment device 150, and the collimator lens 156.

Examples of sections appropriately employed as the horizontal scanning section 142 and the vertical scanning sections 120, 148 include resonant scanners, galvanometer mirrors, polygon mirrors, rotating mirrors, Dove prisms, double Dove prisms, rotation prisms, MEMS mirror scanners, acousto-optical elements (AOM), and the like. In the present exemplary embodiment a galvanometer mirror is employed as the vertical scanning section 148, and a polygon mirror is employed as the vertical scanning sections 120. Note that in cases in which a two-dimensional optical scanner such as a MEMS mirror scanner or the like is employed instead of an optical scanner such as a polygon mirror, a galvanometer mirror, or the like, the relay lens device 140 may be omitted due to being able to perform angle scanning of the incident light in two-dimensions using the reflection elements therein.

The objective lens 130 includes a first lens group 134 and a second lens group 132, in order from the horizontal scanning section 142 side. At least the second lens group 132 is a positive lens group having a positive power overall. In the first exemplary embodiment the first lens group 134 is also a positive lens group having a positive power overall. The first lens group 134 and the second lens group 132 each include at least one positive lens. In cases in which the first lens group 134 and the second lens group 132 each include plural lenses, a negative lens may be included in each of the first lens group 134 or the second lens group 132 as long as each of these lens groups has a positive power overall.

The first lens group 134 and the second lens group 132 configuring the objective lens 130 are separated from each other by a maximum air distance between lens planes of the objective lens along the optical axis. Note that there may be a glass sheet of no power present at a position between the first lens group 134 and the sec and lens group 132. Such a glass sheet is not considered as being a lens belonging to either the first lens group 134 or the second lens group 132, and the first lens group 134 and the second lens group 132 are separated from each other by the maximum air distance.

The image capture optical system 116A includes an anterior eye portion observation-use optical module 136 as an optical module that can be inserted into and removed from the optical path of the objective lens 130, and a sensor 130S to detect the inserted/removed state of the optical module 136. As will be described in detail later, in the first exemplary embodiment, in cases in which the optical module 136 is not disposed on the optical path of the objective lens 130, a posterior eye portion observation optical system 300 (see also FIG. 3) is configured as an observation optical system, and the ophthalmic device 110 acquires an image of the posterior eye portion of the examined eye 12 therewith. However, in cases in which the optical module 136 has been inserted into the optical path of the objective lens 130, an anterior eye portion observation optical system 400 (see also FIG. 4) is configured as the observation optical system, and the ophthalmic device 110 acquires an image of the anterior eye portion of the examined eye 12 therewith. As described in detail later, in the first exemplary embodiment, the optical module 136 is inserted into and removed from the optical path of the observation optical system either manually by an operator (for example, an ophthalmologist) or automatically. The optical module 136 is inserted into the optical path between the first lens group 134 and the second lens group 132, or is removed from the optical path by movement along non-illustrated rails or by rotational movement of a non-illustrated turret. The sensor 130S for detecting the inserted/removed state of the anterior eye portion observation-use optical module 136 may be a sensor that detects either that the optical module 136 has been inserted into the image capture optical system or that the optical module 136 has been removed therefrom, or may be a sensor that detects both states.

The posterior eye portion observation optical system 300 is an example of a "first observation optical system" and of an "ocular fundus observation optical system" of the technology disclosed herein. The anterior eye portion observation optical system 400 is an example of a "second observation optical system" and of an "anterior eye portion observation optical system" of the technology disclosed herein.

In the present exemplary embodiment, a state when observing the examined eye 12 in which the anterior eye portion observation-use optical module 136 is not disposed on the optical path of the image capture optical system is hereafter referred to as a posterior eye portion observation mode (first mode). Moreover, a state when observing the examined eye 12 in which the optical module anterior eye portion observation-use optical module 136 is disposed on the optical path of the image capture optical system is hereafter referred to as an anterior eye portion observation m ode (second mode).

The image capture optical system 116A further includes, as illustrated in FIG. 2, an optical module 138 different from the optical module anterior eye portion observation-use optical module 136. The optical module 138 is mainly employed in the posterior eye portion observation mode, and so is hereafter referred to as a posterior eye portion observation-use optical module 138. Although not illustrated in the drawings, the posterior eye portion observation-use optical module 138 includes an optical module housing 138H including a fixation light, a camera, and an illumination device, and a beam splitter 178. The beam splitter 178 is disposed between the objective lens 130 and the horizontal scanning section 142, and more specifically is disposed on the optical path between the first lens group 134 and the horizontal scanning section 142.

Figure 3:
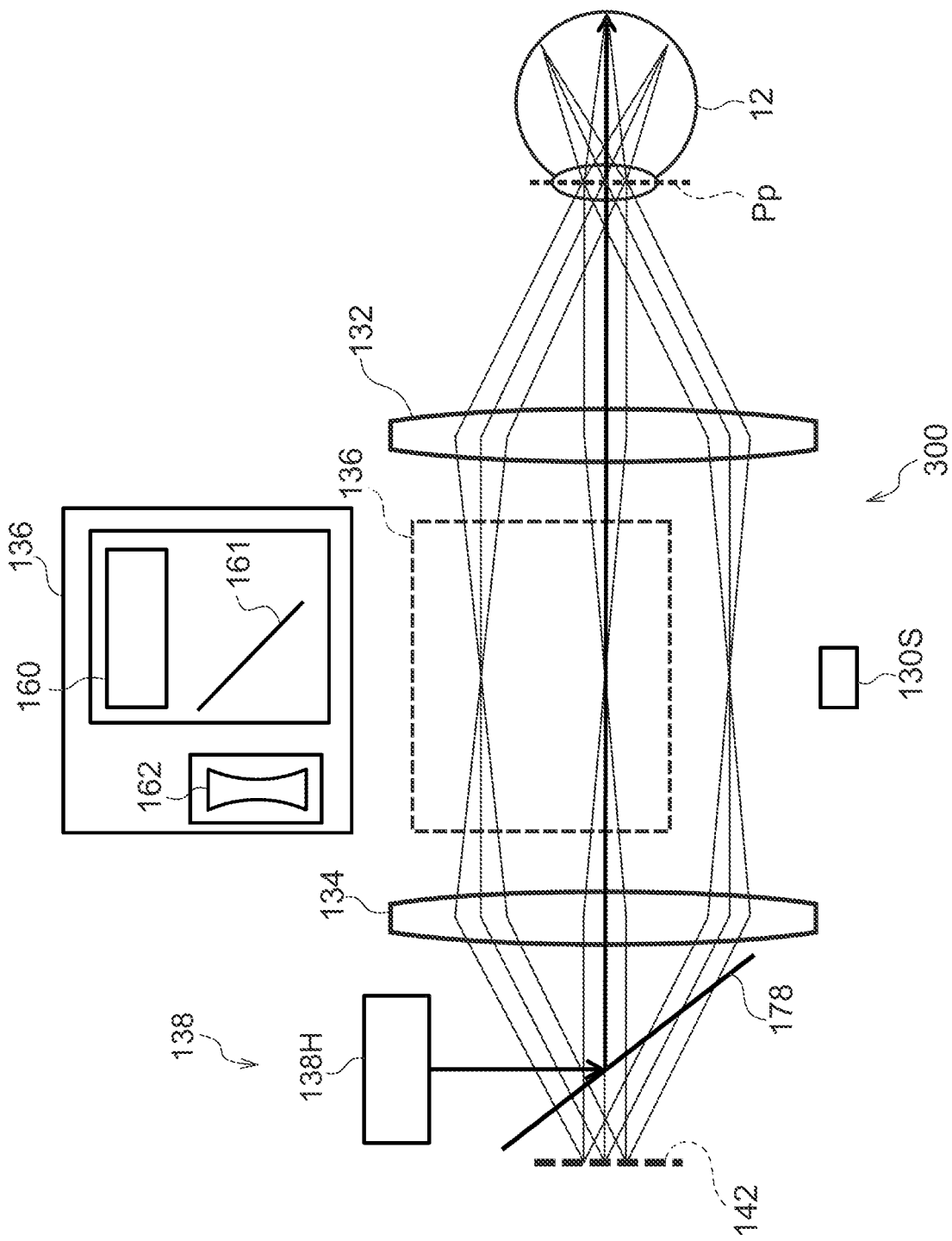
FIG. 3 is a schematic configuration diagram of a partial configuration between a scanning section of an image capture optical system and an examined eye, for a case in which an anterior eye portion observation-use optical module is not inserted on an optical path between a positive first lens group and a positive second lens group.
Figure 4:
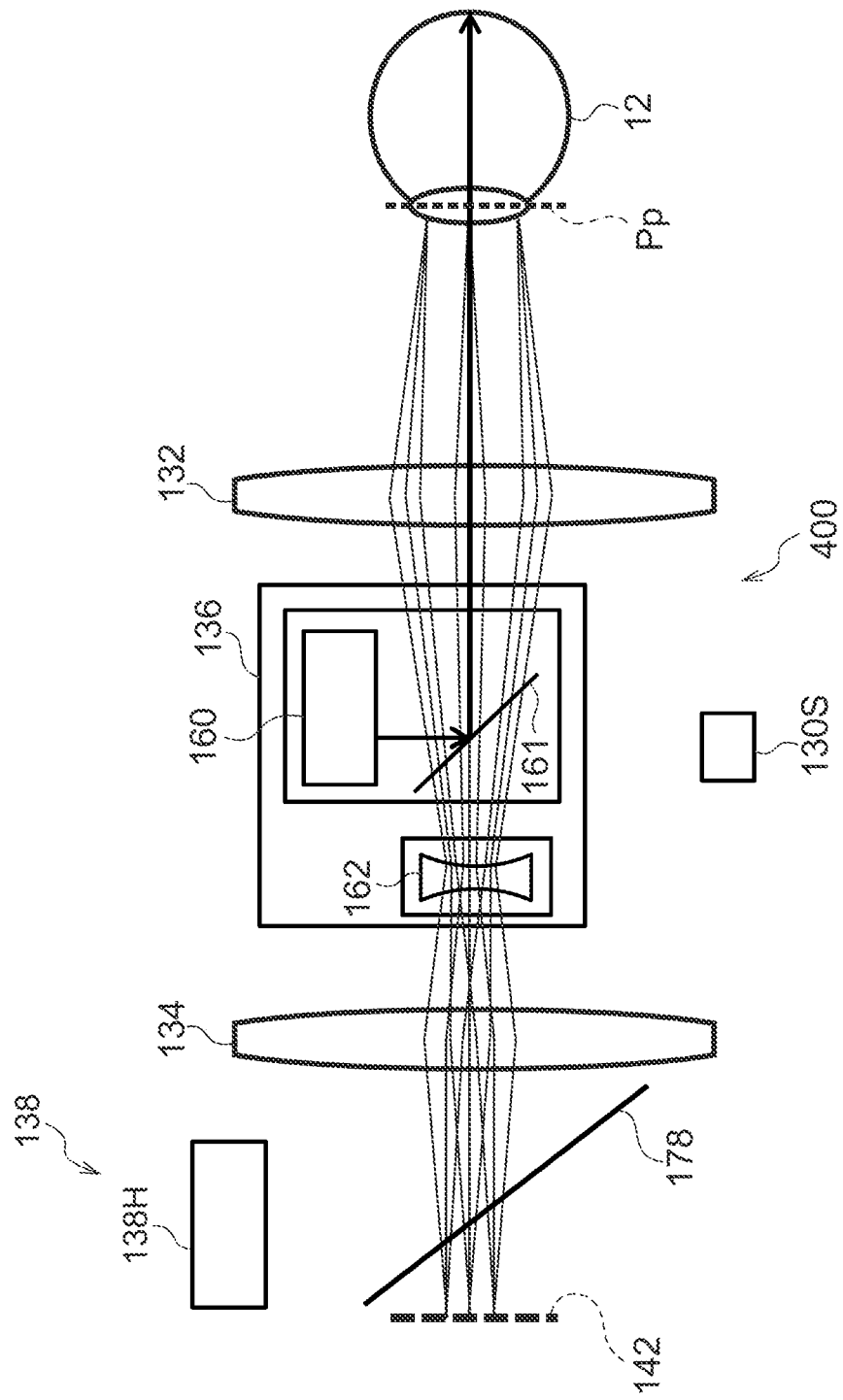
FIG. 4 is a schematic configuration diagram of a partial configuration between a scanning section of an image capture optical system and an examined eye, for a case in which an anterior eye portion observation-use optical module is inserted on an optical path between a positive first lens group and a positive second lens group.

Next, description follows regarding a configuration of the image capture optical system 116A in each of the posterior eye portion observation mode and the anterior eye portion observation mode, with reference to FIG. 3 and FIG. 4. FIG. 3 illustrates the posterior eye portion observation optical system 300 in the posterior eye portion observation mode. The anterior eye portion observation-use optical module 136 is removed from the optical path of the objective lens 130. FIG. 4 illustrates the anterior eye portion observation optical system 400 in the anterior eye portion observation mode. The anterior eye portion observation-use optical module 136 is inserted into the optical path of the objective lens 130, and more specifically is inserted into the optical path between the first lens group 134 on the horizontal scanning sect ion 142 side and the second lens group 132 on the examined eye side. In the posterior eye portion observation optical system 300 (FIG. 3), a pattern of light rays is illustrated for parallel light beams at three angles for parallel light beams supplied from a scanning plane representing the horizontal scanning section 142, passing through two positive lens groups (the first lens group 134 and the second lens group 132), and focused on the ocular fundus 12A of the examined eye 12. Moreover, in the anterior eye portion observation optical system 400 (FIG. 4), light rays are illustrated for parallel light beams at the same three angles supplied from the horizontal scanning section 142, and focused on the cornea of the examined eye 12 by two positive lens groups (the first lens group 134 and the second lens group 132), and by an optical element (a negative lens 162, described in detail later) inserted therebetween.

In the posterior eye portion observation optical system 300, as illustrated in FIG. 3 and FIG. 2, the vertical scanning sections 120, 148 and the horizontal scanning section 142 are arranged so as to be conjugate to a pupil position Pp of the examined eye 12. In the SLO optical system, the SLO laser light scanned by the vertical scanning section 120 and the horizontal scanning section 142, passes through the objective lens 130 and is two-dimensionally angle scanned, with the pupil position Pp of the examined eye 12 at the center. As a result, the focused light point of the SLO laser light is two-dimensionally scanned over the ocular fundus 12A. Similarly thereto, in the OCT optical system, the measurement light scanned by the vertical scanning section 148 and the horizontal scanning section 142, passes through the objective lens 130 and is two-dimensionally angle scanned, with the pupil position Pp of the examined eye 12 at the center. As a result the focused light point of the measurement light is two-dimensionally scanned over the ocular fundus 12A. In the posterior eye portion observation mode for acquiring images by employing the posterior eye portion observation optical system 300, an ocular fundus two-dimensional image is acquired by the SLO unit 18, and an ocular fundus tomographic image is acquired by the OCT unit 20. As described later, during the period of ocular fundus tomographic image acquisition by the OCT unit 20, the SLO unit 18 continuously and successively acquires ocular fundus two-dimensional images.

In the anterior eye portion observation optical system 400, as illustrated in FIG. 4, the anterior eye portion observation-use optical module 136 is inserted into the optical path of the objective lens 130, specifically into the optical path between the first lens group 134 of positive refraction power and the second lens group 132 of positive refraction power that configure the objective lens 130. The optical module 136 includes an internal optical element such as a lens or the like. The optical element in the present exemplary embodiment is the lens 162 having negative power a nd serving as a switching lens. The lens 162 is disposed on the optical axis of the objective lens 130, and the lens 162 operates as a switching lens to switch the posterior eye portion observation optical system 300 into the anterior eye portion observation optical system 400. Hereafter, the lens 162 will sometimes be referred to as the negative lens 162 and sometimes as switching lens 162. In cases in which the negative lens 162 has been inserted into the optical path of the objective lens 130, the scanning position of the horizontal scanning section 142 is not conjugate to the pupil position Pp of the examined eye 12, and the parallel light from the scanning position of the horizontal scanning section 142 is focused on the anterior eye portion. The diameter of the light beam passing through the negative lens 162 is smaller than the respective light beam diameters when passing through the first lens group 134 and the second lens group 132. Thus the effective diameter of the negative lens 162 is smaller than the effective diameter of the lens groups configuring the objective lens 130. The negative lens 162 is smaller than the first lens group 134 and the second lens group 132, enabling the optical module 136 to be made more compact. Note that there is no limitation to employing the negative lens 162 as the optical element, and instead of the negative lens 162, other optical members such as, for example, a Fresnel lens, a Diffractive Optical Element (DOE), or the like may be employed therefor. Moreover, as illustrated in FIG. 3 and FIG. 4, an eye tracking module 160 and a dichromic mirror 161 for use during anterior eye portion observation are inbuilt into the anterior eye portion observation-use optical module 136. The plural SLO images successively acquired by the SLO unit are utilized as images for eye tracking during OCT imaging using the eye tracking module 160 in-built into the anterior eye portion observation-use optical module 136.

The eye tracking module 160 moreover also includes a non-illustrated fixation light, camera, and illumination device.

Next, description follows regarding optical configuration in the posterior eye portion observation mode and in the anterior eye portion observation mode. The top diagram in FIG. 5 schematically illustrates a posterior eye portion observation optical system in the posterior eye portion observation mode (first mode). The anterior eye portion observation-use optical module 136 is not inserted into the optical path of the objective lens 130. The bottom diagram in FIG. 5 schematically illustrates an anterior eye portion observation optical system in the anterior eye portion observation mode (second mode). The optical module 136 with in-built negative switching lens 162 is inserted into the optical path of the objective lens 130. Note that, for ease of explanation, only the switching lens 162 is illustrated as the optical module 136 in the schematic diagram of the anterior eye portion observation optical system.

Description follows regarding the posterior eye portion observation optical system (FIG. 5 top diagram). In the posterior eye portion observation optical system (FIG. 5 top diagram), plural lens groups configuring the objective lens 130, namely the positive first lens group 134 and the positive second lens group 132, form an afocal system, with the scanning center of the horizontal scanning section 142 (Ps in the diagram) conjugate to the pupil position Pp of the examined eye 12. In this configuration d=f1+f2, wherein f1 and f2 are the respective focal distances of the first lens group 134 and the second lens group 132, and d is the distance between the first lens group 134 and the second lens group 132 (inter-group separation). Magnification β is defined by:

β=-f2/f1

In the posterior eye portion observation mode (first mode) of the first exemplary embodiment, a scanning position Ps of the horizontal scanning section 142 is conjugate to the pupil position Pp of the examined eye 12. Parallel light from the scanning position Ps of the horizontal scanning section 142 passes as substantially parallel light at a specific angle through the pupil position Pp of the examined eye 12, and is focused on the ocular fundus 12A by the examined eye 12. The position of focused light on the ocular fundus 12A of the measurement light emitted from the OCT unit 20 is determined depending on the scanning position of the vertical scanning section 120 and the scanning angle at the scanning position (Ps) of the horizontal scanning section 142. This thereby enables a desired scanning position and scanning range to be set for imaging and observation of the ocular fundus 12A.

Next, description follows regarding the anterior eye portion observation optical system (FIG. 5 bottom diagram). In this observation optical system, the switching lens 162 of the anterior eye portion observation-use optical module 136 is inserted into the optical path of the objective lens 130.

In the anterior eye portion observation mode (second mode), the switching lens 162 that is a negative lens is inserted between the first lens group 134 and the second lens group 132. In the anterior eye portion observation mode (second mode), the scanning position Ps of the horizontal scanning section 142 is not conjugate to the pupil position Pp of the examined eye 12, and parallel light from the scanning position Ps of the horizontal scanning section 142 is focused on the anterior eye portion. The position of focused light on the anterior eye portion of the measurement light emitted from the OCT unit 20 is determined depending on the scanning angle at the position (Ps) of the scanning section. This thereby enables anterior eye portion observation to be performed.

Description follows regarding placement of the switching lens 162 in the anterior eye portion observation mode (second mode). f3 denotes the focal distance of the switching lens 162, x denotes the distance between the first lens group 134 and the switching lens 162, S3 denotes the object distance from the switching lens 162 when parallel light from the scanning position Ps is introduced to the first lens group 134, and S3' denotes the image distance of the switching lens 162. Note that the image position P3' in the drawings is the image position of the scanning position Ps by the switching lens 162 when parallel light from the scanning position Ps is introduced to the first lens group 134, namely, a conjugate position of the scanning position Ps due to the switching lens, and image position P3' is conjugate to the pupil position Pp of the examined eye 12.

The following is obtained from the image formation equation for the switching lens 162.

$$\frac{1}{S3'} = \frac{1}{S3} + \frac{1}{f3}$$

The following is obtained from S3=f1-x.

$$S3' = \frac{f3(f1-x)}{f1+f3-x} \quad (1)$$

Next, similarly for the second lens group 132, S2 denotes the object distance of the second lens group 132 when parallel light from the scanning position Ps is introduced to the first lens group 134, S2' denotes the image distance, and the following is obtained from the image formation equation of the second lens group 132.

$$\frac{1}{S2'} = \frac{1}{S2} + \frac{1}{f2}$$

Note that in practice ST is the distance between the second lens group 132 and the examined eye 12, the so-called working distance (WD). Moreover, as is apparent from FIG. 5, $$S2 = S3' + d - x.$$

Hence $$\frac{1}{S2'} = \frac{1}{S3' + d - x} + \frac{1}{f2} \quad (2)$$

Substituting Equation (1) into Equation (2) yields $$\frac{f2 - S2'}{f2 \times S2'} = \frac{f1 + f3 - x}{f3(f1 - x) + (f1 + f3 - x)(d - x)} \quad (3)$$

Rearranging Equation (3) for x yields the following equation.

$$x^2 - \left(2f1 + f2 + 2f3 + \frac{S2' \times f2}{S2' + f2}\right)x +$$
$$(f1 + f2)(f1 + f3) + f1 \times f3 + \frac{S2 \times f2}{S2' - f2}(f1 + f3) = 0 \quad (4)$$

Deciding the focal distance f3 of the switching lens 162 enables the value of position x to be found using this Equation (4).

Note that in cases in which the light between the two positive groups of the first lens group 134 and the second lens group 132 is parallel light, then f2=ST. Hence, the simplified Relationship Equation (5) follows from Equation (3):

$$x = f1 + f3 \quad (5)$$

By approximation, a configuration can be adopted in which the switching lens 162 is disposed between the first lens group 134 and the second lens group 132 under Relationship Equation (5). The Relationship Equation (5) applies to cases in which the two positive groups of the first lens group 134 and the second lens group 132 configure a completely afocal system, and moreover in which the light between the two groups is completely parallel light, so may be said to be an ideal configuration. In practice, the shape, thickness, refractive index etc. of each of the lenses should obviously be appropriately selected to make a substantially parallel system between the two lens groups, and to achieve a favorable aberration structure in both the posterior eye portion observation mode (first mode) and the anterior eye portion observation mode (second mode) according to a suitable aberration calculation.

In the first exemplary embodiment, as illustrated in FIG. 5, the distance between the second lens group 132 and the examined eye 12 (working distance WD) does not change whether in the posterior eye portion observation mode (first mode) or in the anterior eye portion observation mode (second mode). Thus there is no need to re-adjust the alignment of the examined eye 12 and the image capture optical system 116A according to changes in observation mode, and accordingly no need to compel the subject of examination to move. The time required to capture a series of images is accordingly shortened due to being able to switch smoothly and speedily between anterior eye portion imaging and posterior eye portion imaging. In addition, due to the switching lens 162 being small, a mechanism to insert/remove the switching lens 162 can also be realized by a simple and compact mechanism.

In the ophthalmic device 110 according to the first exemplary embodiment as described above, employing the anterior eye portion observation-use optical module 136 enables a device to be provided for acquiring three-dimensional image data for both a posterior eye portion and an anterior eye portion of the examined eye 12 with a single ophthalmic device.

Moreover, the ophthalmic device 110 of the first exemplary embodiment is switchable between the posterior eye portion observation optical system and the anterior eye portion observation optical system by insertion or removal of the anterior eye portion observation-use optical module 136 into the optical path between the first lens group 134 and the second lens group 132 configuring of the objective lens 130. The working distance WD between the objective lens 130 (and in particular the second lens group 132) and the examined eye 12 accordingly does not change in the respective optical systems (300, 400). This enables switching to be performed smoothly between the posterior eye portion observation mode and the anterior eye portion observation mode due to not needing to redo the alignment between the examined eye 12 and the image capture optical system 116A.

Moreover, in the ophthalmic device 110 according to the first exemplary embodiment, the optical element of the anterior eye portion observation-use optical module 136 is a small lens having a smaller effective diameter than the effective diameter of the objective lens 130 (the first lens group 134 and the second lens group 132), enabling the optical module 136 to be made more compact. This accordingly enables switching to be made simply between the posterior eye portion observation-use optical system and the anterior eye portion observation optical system.

The above features enable the convenience of the ophthalmic device 110 to be raised in the first exemplary embodiment.

Next, description follows regarding a modified example of the first exemplary embodiment.

Figure 6:
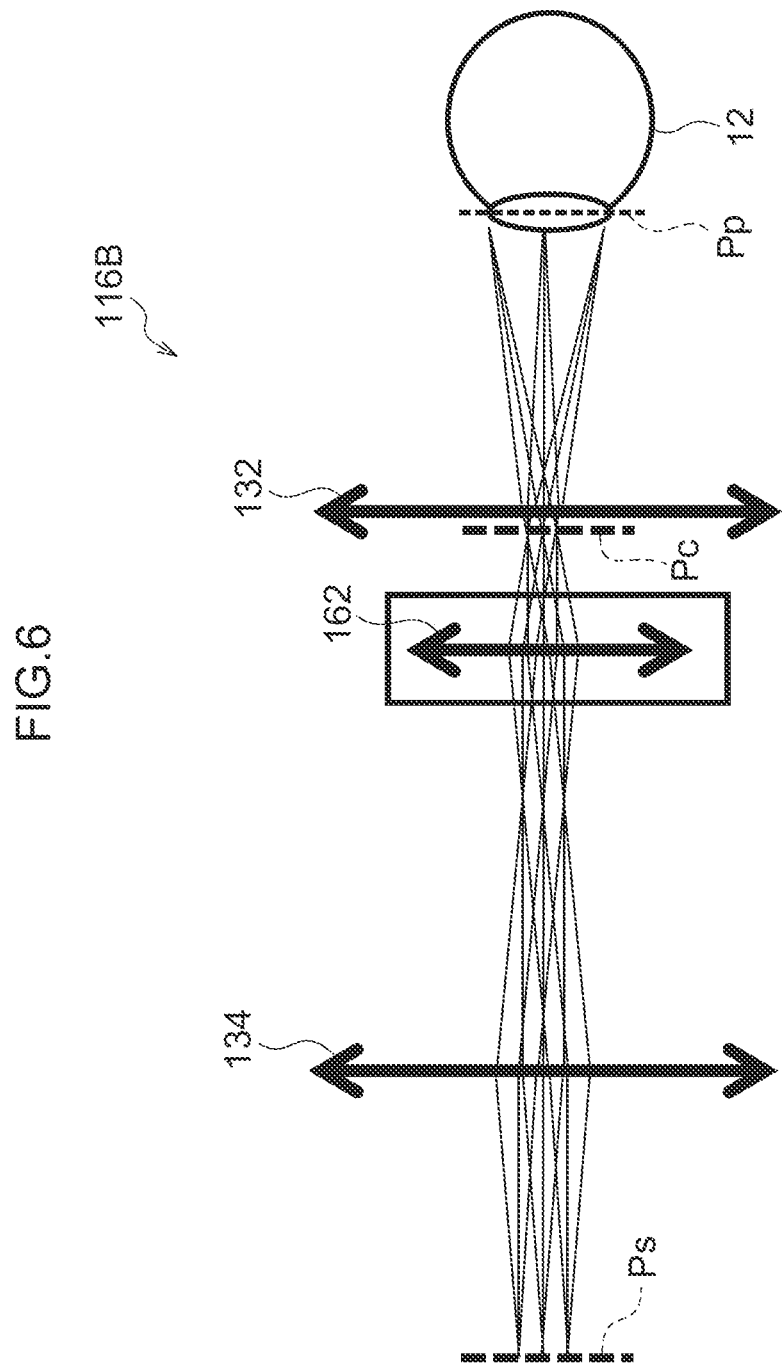
FIG. 6 is an optical configuration diagram using a thin system to illustrate a basic configuration of an image capture optical system of a modified example of the first exemplary embodiment.

Although the first exemplary embodiment includes a negative lens as the switching lens 162, technology disclosed herein is not limited thereto. The switching lens 162 may be a lens having a positive power (positive lens). FIG. 6 illustrates a schematic optical configuration of an objective lens that is a main section in an image capture optical system 116B equipped with a positive lens as the switching lens 162. In such cases, the position Pc conjugant to the scanning position Ps of the horizontal scanning section 142 is positioned beside the second lens group 132, as illustrated in FIG. 6. FIG. 6 is an optical configuration of an anterior eye portion image capture optical system in anterior eye portion observation mode that is a state in which the anterior eye portion is being imaged, and corresponds to the bottom diagram of aforementioned FIG. 5. In this configuration the optical configuration of the posterior eye portion observation mode (first mode), which is a state in which the posterior eye portion is being imaged, corresponds to the top diagram in FIG. 5 (posterior eye portion observation optical system 300). Similarly to in FIG. 5, the lens groups are illustrated using a thin system in FIG. 6, and a pattern is schematically illustrated of parallel light beams at three angles from the scanning position Ps of the horizontal scanning section 142 being focused at an anterior eye portion of the examined eye.

Although in the first exemplary embodiment an operator manually removes the anterior eye portion observation-use optical module 136 from the optical path of the image capture optical system 116A and manually inserts the optical module 136 into the optical path, the technology disclosed herein is not limited thereto. For example, a mechanism may be provided to automatically remove the anterior eye portion observation-use optical module 136 from the optical path, or to automatically insert the optical module 136 into the optical path. In cases in which a non-illustrated posterior eye portion tomographic image generation button has been switched ON, or in cases in which a non-illustrated anterior eye portion tomographic image gene ration button has been switched ON, the CPU 16A may control such a mechanism so as to automatically remove the anterior eye portion observation-use optical module 136 from the optical path or to automatically insert the optical module 136 into the optical path.

Although in the first exemplary embodiment the objective lens 130, the horizontal scanning section 142, and the relay lens device 140 are employed in order from the examined eye 12 side as a common optical system that is common to the SLO optical system and the OCT optical system, the technology disclosed herein is not limited thereto. Instead of the configuration in which the horizontal scanning section 142 employed is common to the SLO optical system and the OCT optical system, a horizontal scanning section and a vertical scanning section may be provided to each respective optical system.

Second Exemplary Embodiment

Next, description follows regarding a second exemplary embodiment. The configuration of the second exemplary embodiment is substantially the same as that of the first exemplary embodiment, and so the same reference numerals are appended to same sections and description thereof will be omitted, and mainly the different sections thereof described.

Figure 7:
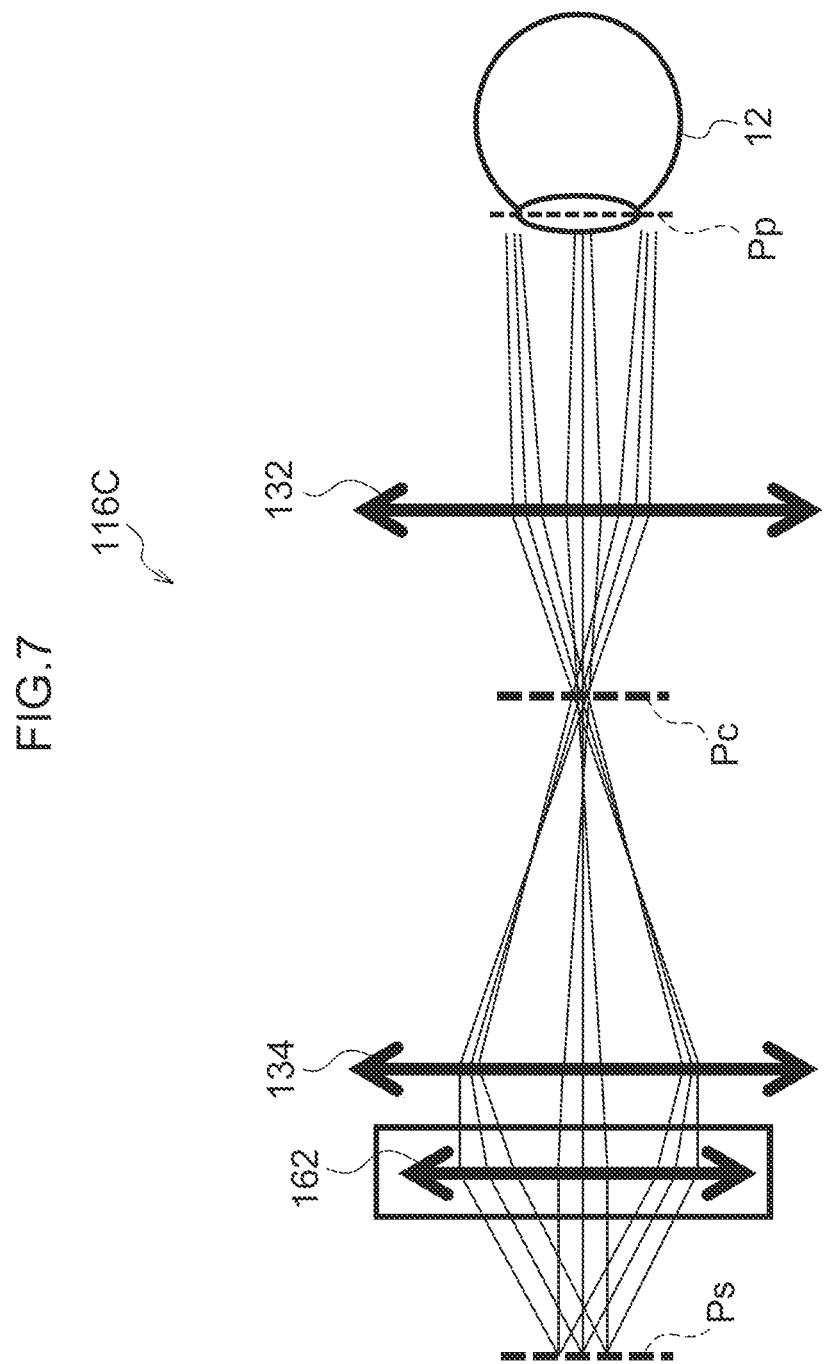
FIG. 7 is an optical configuration diagram using a thin system to illustrate a basic configuration of an image capture optical system of a second exemplary embodiment.

FIG. 7 illustrates a schematic optical configuration of an objective lens that is a main section in an image capture optical system 116C of the second exemplary embodiment. The image capture optical system 116C differs from the image capture optical system 116A of the first exemplary embodiment in the following manner.

The switching lens 162 inserted in the image capture optical system 116C is arranged so as to be capable of being inserted between the first lens group 134 and the horizontal scanning section 142 or removed therefrom, rather than between the first lens group 134 and the second lens group 132 configuring the objective lens 130. As illustrated in FIG. 7, a configuration is illustrated of an anterior eye portion observation optical system in which a lens having a positive power is employed as the switching lens 162 in an anterior eye portion observation mode. A position Pc conjugate to the scanning position Ps of the horizontal scanning section 142 is positioned between the first lens group 134 and the second lens group 132.

Figure 8:
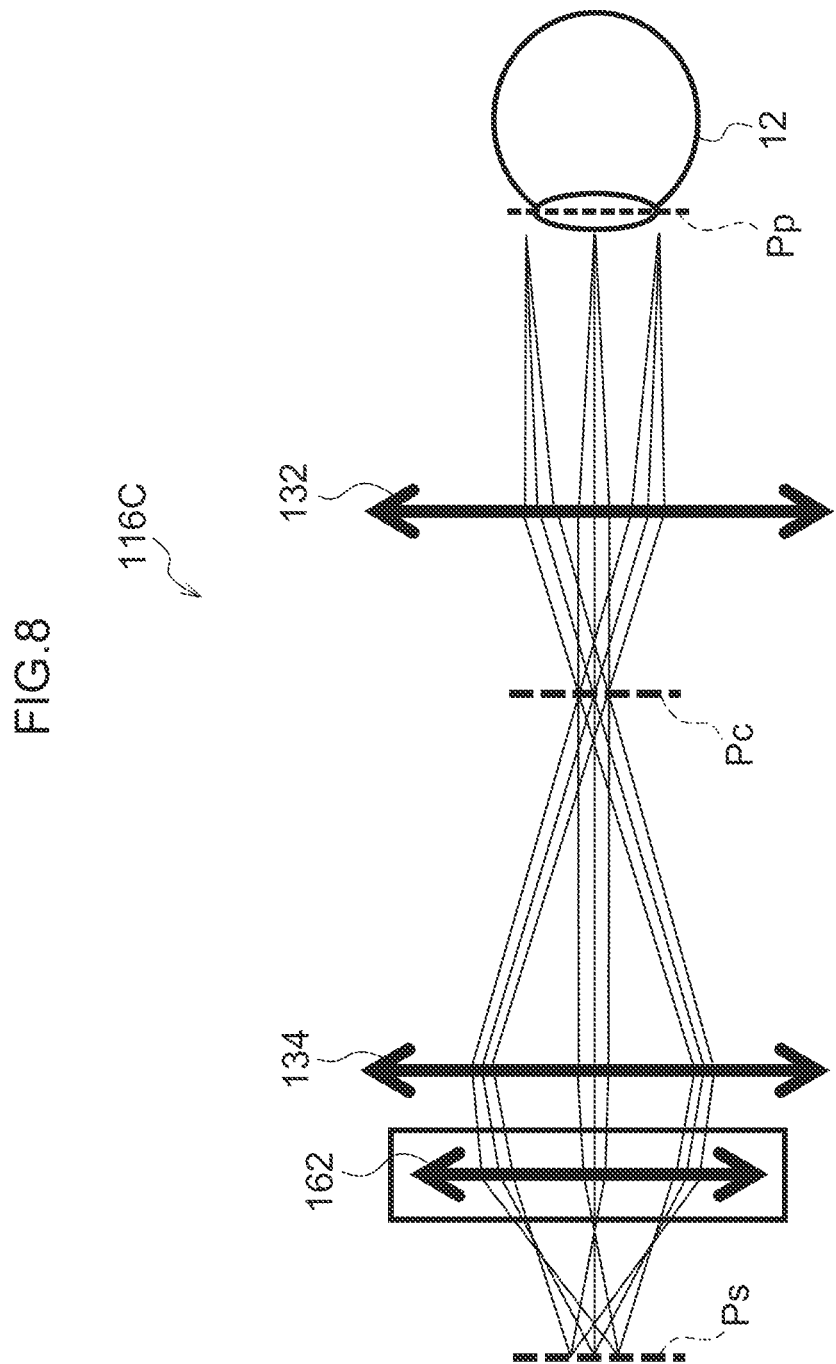
FIG. 8 is an optical configuration diagram using a thin system to illustrate a pattern more focused at an anterior eye portion of an examined eye for light in an image capture optical system of the second exemplary embodiment.

The posterior eye portion observation optical system of the posterior eye portion observation mode employed for ocular fundus imaging is similar to that of the top diagram in FIG. 5. In the configuration of FIG. 7, the scanning light of parallel light beams from the horizontal scanning section 142 can be focused in the vicinity of the anterior eye portion of the examined eye 12 by inserting the switching lens 162. However, in order to completely focus on the anterior eye portion of the examined eye, a focusing device, for example the focus adjustment device 150 illustrated in FIG. 2, is controlled so as to be able to appropriately focus light at the required position in the anterior eye portion of the examined eye 12 by converting the light beams introduced into the scanning section into appropriately focused light, as illustrated in FIG. 8.

Figure 9:
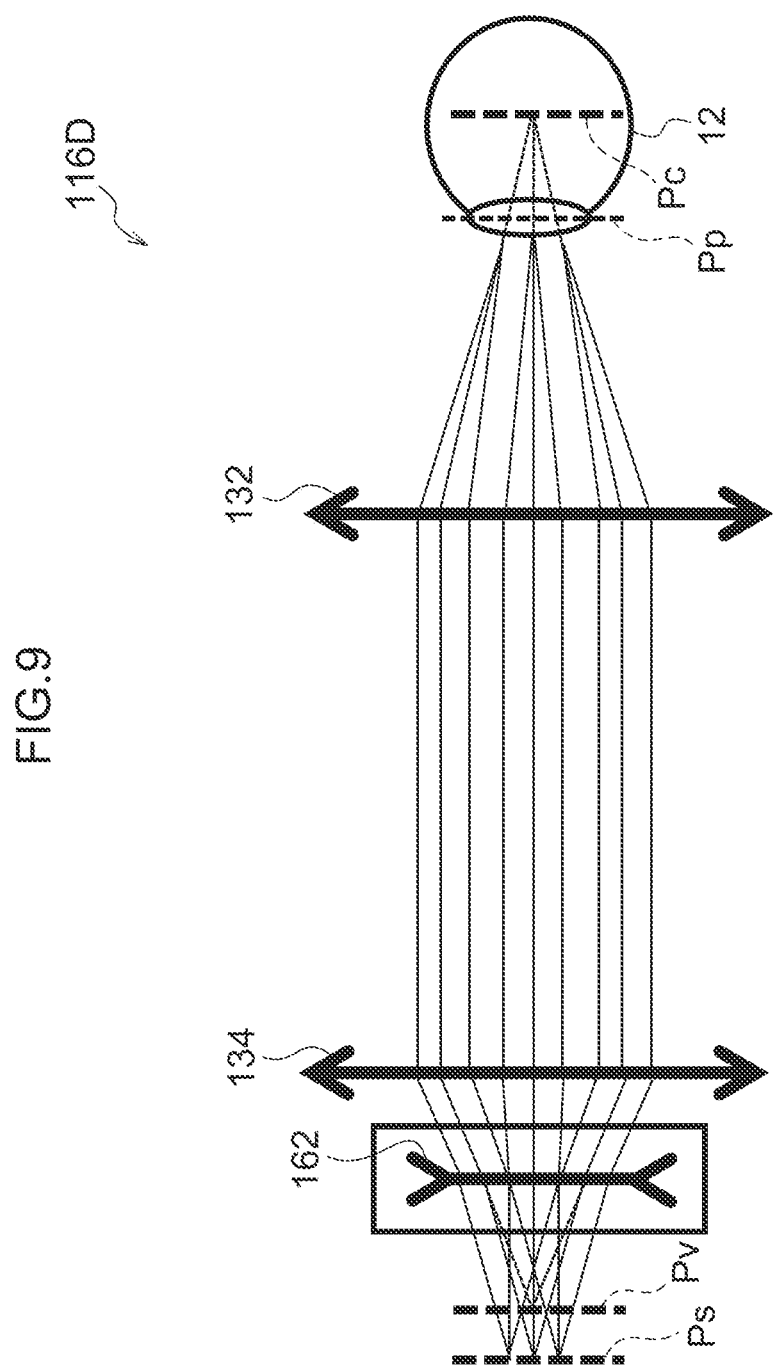
FIG. 9 is an optical configuration diagram using a thin system to illustrate a basic configuration of an image capture optical system of a further modified example of the second exemplary embodiment.

Next, description follows regarding a modified example of the second exemplary embodiment. Although in the second exemplary embodiment a lens having a positive power is employed as the switching lens 162, the technology disclosed herein is not limited thereto. A negative lens may be employed as the switching lens 162. FIG. 9 illustrates an example of an image capture optical system 116D equipped with a lens having a negative power as the switching lens 162. FIG. 9 illustrates pattern of light rays in a configuration of the anterior eye portion observation mode (second mode) in a state for imaging the anterior eye portion with the lens having a negative power employed as the switching lens 162 inserted between the scanning position Ps of the horizontal scanning section 142 and the first lens group 134 of the objective lens 130. As illustrated in the drawing, parallel light beams introduced from the center of the horizontal scanning section 142 are focused on the cornea as the anterior eye portion of the examined eye 12 by the switching lens 162, the first lens group 134 having a positive power, and the second lens group 132 having a positive power. In the anterior eye portion observation mode (second mode), a virtual image Pv of position PS of the horizontal scanning section 142 is formed by the switching lens 162, which is a lens having a negative power, between the scanning position Ps of the horizontal scanning section 142 and the negative switching lens 162. The position Pc conjugate to the scanning position Ps of the horizontal scanning section 142 is formed inside the examined eye 12 by the combined optical system configured by the lens 162 having a negative power, the first lens group 134, and the second lens group 132, however, there is no limitation thereto. Obviously a posterior eye portion observation mode (first mode) that is the same as the configuration illustrated in the diagram at the top portion of FIG. 5 may be achieved by removing the switching lens 162 from the configuration of the anterior eye portion observation mode (second mode) illustrated in FIG. 9.

Third Exemplary Embodiment

Next, description follows regarding a third exemplary embodiment. In the configuration of the third exemplary embodiment the same reference numerals are appended to sections corresponding those of FIG. 5 illustrating the first exemplary embodiment, and detailed description thereof will be omitted, with mainly the different sections thereof described.

First, although in the first exemplary embodiment to the modified example of the second exemplary embodiment the objective lens 130 is configured by two lens groups each having a positive power, the technology disclosed herein is not limited thereto. The first lens group 134 employed at the horizontal scanning section 142 side, namely, at the scanning position Ps side, may be configured by a lens group having a negative power.

As illustrated in FIG. 10, an image capture optical system 116E of the third exemplary embodiment includes a first lens group 134N having a negative power in stead of the first lens group 134 having a positive power of the image capture optical system 116A of the first exemplary embodiment. A configuration of an anterior eye portion observation optical system in an anterior eye portion observation mode f or anterior eye portion imaging is illustrated in the top diagram of FIG. 10, and a configuration of a posterior eye portion observation optical system in a posterior eye portion observation mode for posterior eye portion imaging by insertion of a switching lens is illustrated in the bottom diagram of FIG. 10, with both configurations illustrated by using a thin system.

First, in the configuration illustrated in the top diagram of FIG. 10, the parallel light beams from the scanning position Ps of the horizontal scanning section 142 are focused at the pupil position Pp of the examined eye 12 by an objective lens configured by two groups, a first lens group 134N having a negative power and a second lens group 132 having a positive power. This state is a state in which the switching lens 162 has been removed from the optical path. The configuration illustrated in the bottom diagram of FIG. 10 illustrates a configuration of a posterior eye portion observation optical system in a posterior eye portion observation mode, and illustrates a state in which a switching lens 162 having a positive power has been inserted into the optical path of the objective lens between the first lens group 134N having negative power and the second lens group 132 having a positive power. In this state, the parallel light beams supplied from the scanning position Ps of the horizontal scanning section 142 are made into parallel light beams at the pupil position Pp of the examined eye by the combined system configured by the first lens group 134N having a negative power, by the switching lens 162 having a positive power, and by the second lens group 132 having a positive power, so as to form an overall afocal system. The scanning position Ps of the horizontal scanning section 142 and the pupil position Pp of the examined eye 12 are configured so as to be conjugate to each of her, and the parallel light beams at the pupil position Pp of the examined eye 12 are angle-scanned according to angle scanning of the light beams by the scanning section, and the focused light is scanned over the ocular fundus. Note that in the bottom diagram of FIG. 10 only the switching lens 162 from out of the optical module 136 is illustrated. The conjugate position to the ocular fundus is illustrated here by the broken line Cr, and the conjugate position to the examined eye ocular fundus is formed between the inserted switching lens 162 having a positive power and the second lens group 132 having a positive power.

In the image capture optical system of the third exemplary embodiment, imaging of an anterior eye portion is possible in the state illustrated in the top diagram of FIG. 10 in which the optical module 136 has not been inserted, and imaging of a posterior eye portion is possible in the state illustrated in the bottom diagram of FIG. 10 in which the optical module 136 has been inserted. Thus the optical module 136 in such cases is a posterior eye portion-use switching module.

Focus adjustment like that of the second exemplary embodiment may also be performed in the first exemplary embodiment, the modified example of the first exemplary embodiment, the modified example of the second exemplary embodiment, and the third exemplary embodiment that have been described above. Furthermore, the focus adjustment may also be performed in each of the examples by the autofocusing as described above. The focus adjustment may be performed by moving at least one element of the optical system further to the light source side than the second lens group 132 of the objective lens, such as, for example, the first lens group 134, the switching lens 162, or the lenses 144, 146 of the objective lens. Adopting the above exemplary embodiment has the significant advantage described above of enabling a tomographic image of the anterior eye portion to be generated without shifting the position of the examined eye 12 from the position when generating a tomographic image of a posterior eye portion, and, in reverse, not needing to change to the position of the examined eye at all when switching from generating a tomographic image of the anterior eye portion to generating a tomographic image of the posterior eye portion.

Further Modified Examples

In addition to the examples described above, a configuration may be adopted in which plural optical elements of different powers, such as switching lenses, are prepared, and then, according to the pre-acquired shape of the anterior eye portion (for example, the cornea), an optical element from out of the plural optical elements is switched to the optical element that is capable of better focusing light at the corneal position according to the shape etc. of the cornea.

In addition to the examples described above, a configuration may be adopted in which, according to the shape of the anterior eye portion (for example, the cornea), not only is the position of insertion of an optical element, such as a switching lens or the like, switchable to a position between the first lens group 134 and the sec and lens group 132, or to a position between the horizontal scanning section 142 and the first lens group 134, but also, from out of plural optical elements of different powers, such as switching lenses or the like, an optical element of different refractive power may be selected and then inserted at the appropriate switching position.

In addition, although in the examples described above, interference light is detected with a single detector in both the posterior eye portion observation mode (first mode) and the anterior eye portion observation mode (second mode), the technology disclosed herein is not limited thereto. For example, two detectors having different detection abilities may be provided, with one detector from out of the two detectors used to detect interference light in the posterior eye portion observation mode (first mode), and the other detector from out of the two detectors used to detect interference light in the anterior eye portion observation mode (second mode).

The invention claimed is:

1. An ophthalmic device comprising:
   a scanning member for scanning light that has been emitted from a light source;
   an objective lens comprising a first lens group and a second lens group in order from the scanning member side, the first lens group of the objective lens being a lens group having a positive power, and the second lens group being a lens group having a positive power; and
   an optical element that is capable of being inserted into and removed from an optical path between the first lens group of the objective lens and the second lens group of the objective lens, the optical element being a lens having a negative power, wherein:
   in a case in which the optical element is not inserted into the optical path, the objective lens configures a first observation optical system, and light that is scanned by the scanning member is focused in a first region of an examined eye, and
   in a case in which the optical element has been inserted into the optical path, the objective lens and the optical element configure a second observation optical system, and light that is scanned by the scanning member is focused in a second region that is different from the first region of the examined eye.

2. The ophthalmic device according to claim 1, wherein:
the first observation optical system configures an ocular fundus observation optical system of an afocal system, and the first region is a posterior eye portion of the examined eye; and
the second observation optical system configures an anterior eye portion observation optical system, and the second region is an anterior eye portion of the examined eye.

3. The ophthalmic device according to claim 1, wherein the optical element is capable of being inserted into and removed from between the scanning member and the first lens group.

4. The ophthalmic device according to claim 1, further comprising a focus lens that adjusts a focus position in an optical axis direction of the light that has been emitted from the light source.

5. An optical tomographic image generation device, comprising:
a light source that generates light for optical coherence tomography (OCT);
a dividing section that divides light from the light source into measurement light and reference light;
a scanning member for scanning the measurement light;
an objective lens comprising a first lens group and a second lens group in order from a scanning member side, the first lens group of the objective lens being a lens group having a positive power, and the second lens group being a lens group having a positive power;
an optical element that is capable of being inserted into and removed from an optical path between the second lens group of the objective lens and the first lens group of the objective lens, the optical element being a lens having a negative power;
an interference light detector that detects interference light obtained by synthesis of return light from an examined eye and the reference light; and
an image generation section that generates a tomographic image of the examined eye based on the interference light detected by the interference light detector, wherein:
in a case in which the optical element is not inserted into the optical path, the objective lens configures a first observation optical system, and light that is scanned by the scanning member is focused in a first region of the examined eye, and
in a case in which the optical element has been inserted into the optical path, the objective lens and the optical element configure a second observation optical system, and light that is scanned by the scanning member is focused in a second region of the examined eye.

6. The optical tomographic image generation device according to claim 5, further comprising:
a laser light source that generates laser light for a scanning laser ophthalmoscope (SLO); and
a laser light detector that detects laser light that has been reflected at an ocular fundus of the examined eye,
wherein the laser light is irradiated to the ocular fundus of the examined eye via the objective lens.

* * * * *